United States Patent
Merkel et al.

(12) 
(10) Patent No.: US 6,274,779 B1
(45) Date of Patent: Aug. 14, 2001

(54) PURIFIED 1,1,1,3,3,3-HEXAFLUOROPROPANE AND METHOD FOR MAKING SAME

(76) Inventors: Daniel Christopher Merkel, 64 Glenmar Dr., West Seneca, NY (US) 14224; Addison Miles Smith, 80 Berryman Dr., Amherst, NY (US) 14226; Kim Marie Fleming, 3617 Center Lane Dr., Hamburg, NY (US) 14075

( * ) Notice: Subject to any disclaimer, the term of this patent is extended or adjusted under 35 U.S.C. 154(b) by 0 days.

(21) Appl. No.: 09/513,899

(22) Filed: Feb. 28, 2000

Related U.S. Application Data

(60) Continuation of application No. 09/165,732, filed on Oct. 2, 1998, now abandoned, which is a division of application No. 09/040,254, filed on Mar. 3, 1998, now Pat. No. 5,856,595.

(51) Int. Cl.[7] .................................................. C07C 19/08
(52) U.S. Cl. ................................................ 570/134
(58) Field of Search .................................. 570/134, 178

(56) References Cited

U.S. PATENT DOCUMENTS

| | | |
|---|---|---|
| 4,948,479 | 8/1990 | Brooks et al. |
| 5,718,807 * | 2/1998 | Miller et al. ........................ 570/178 |
| 5,856,595 * | 1/1999 | Merkel et al. ....................... 570/178 |

FOREIGN PATENT DOCUMENTS

WO98 00378    8/1998   (WO).

* cited by examiner

*Primary Examiner*—Alan Siegel
(74) *Attorney, Agent, or Firm*—Colleen D. Szuch

(57) ABSTRACT

A 1,1,1,3,3,3-hexafluoropropane product of greater than about 99.9 weight percent purity containing less than about 100 parts per million unsaturated fluorocarbons and a method for its purification from a distillation mixture of 1,1,1,3,3,3-hexafluoropropane with at least one unsaturated fluorocarbon which method includes the steps of:

a) reacting the mixture with chlorine to saturate the unsaturated fluorocarbons, b) washing the reacted mixture with an aqueous solution to remove residual hydrochloric acid and chlorine, c) removing the aqueous solution, and d) distilling the reacted mixture to obtain a 1,1,1,3,3,3-hexafluoropropane product of greater than about 99.9 weight percent purity containing less than about 100 parts per million unsaturated fluorocarbons.

1 Claim, 1 Drawing Sheet

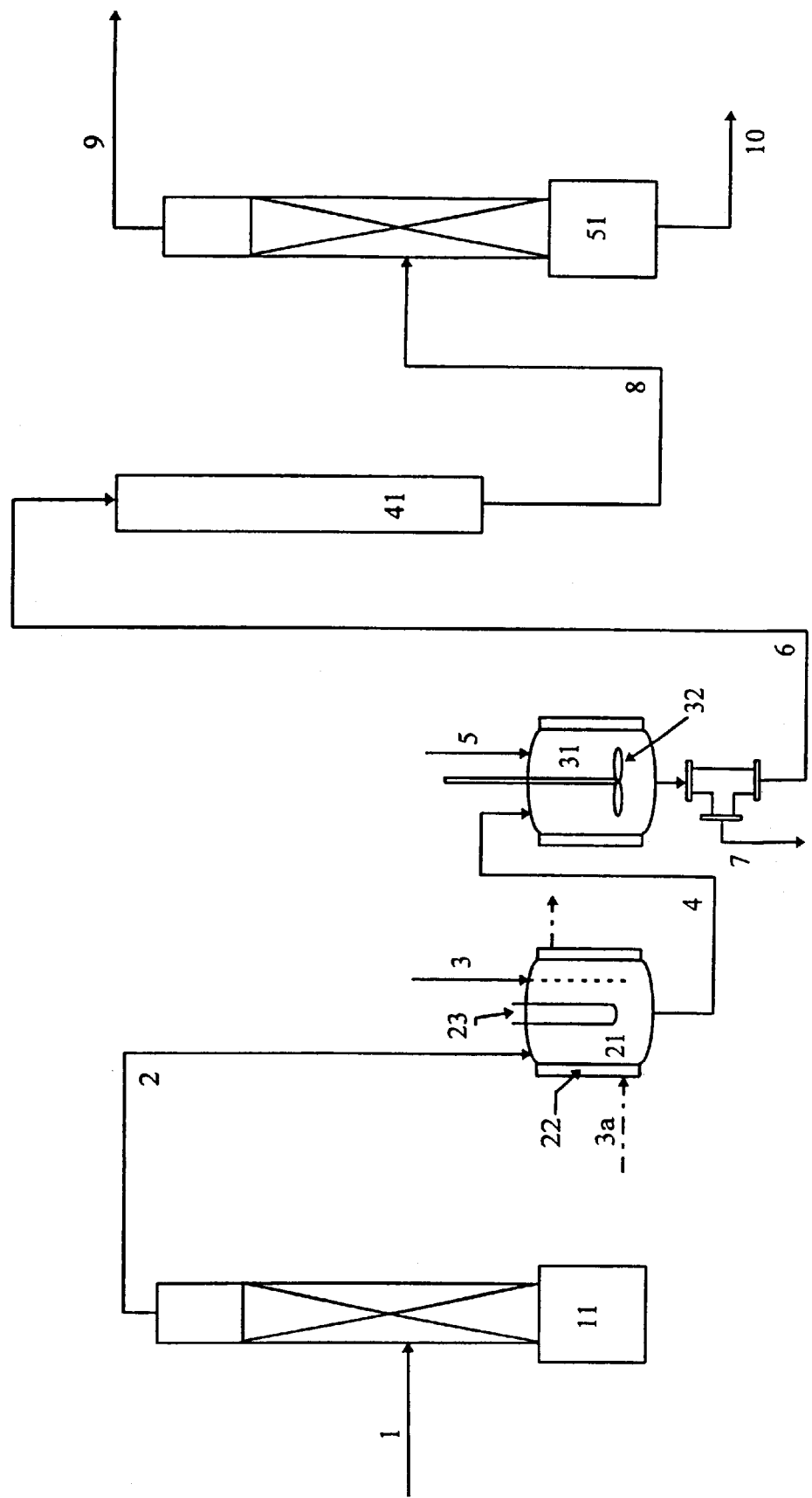

PURIFIED 1,1,1,3,3,3-HEXAFLUOROPROPANE AND METHOD FOR MAKING SAME

This application is a continuation of Ser. No. 09/165,732 filed Oct. 2, 1998 now abandoned which is a division of Ser. No. 09/040,254 filed Mar. 3, 1998 now U.S. Pat. No. 5,856,595

BACKGROUND OF THE INVENTION

This invention relates to fluorocarbons for use as refrigerants and more particularly relates to fluorocarbon 1,1,1,3,3,3-hexafluoropropane (EFC-236fa) and methods for its purification.

Due to their stability, relatively low toxicity, compatibility with numerous substances, and low vaporization points, short chain fluorocarbons have been found to have utility or potential utility in industry for many purposes. Such short chain fluorocarbons (about 1 to about 5 carbon atoms) have, for example, been used as propellants, refrigerants, and solvents.

It has been asserted that certain fluorocarbons, especially chlorofluorocarbons, unfortunately may be hazardous to the environment, especially to the ozone layer. Further, impurities in certain fluorocarbons have been found to be troublesome. Unsaturated fluorocarbons are especially undesirable since many of them are toxic and are also often unstable. Such unstable unsaturated fluorocarbons can decompose into even more undesirable products which can be corrosive. It is therefore especially important that fluorocarbons be essentially free (e.g. less than 500 ppm) of unsaturated species. There has therefore been a concerted effort to develop new and purer fluorocarbons which are viewed as being more environmentally friendly.

With respect to some fluorocarbons, it has been found possible to reduce the quantity of unsaturated species by chlorination, e.g. as described in U.S. Pat. Nos. 5,190,626 and 5,336,377. Unfortunately the outcome of such a chlorination technique is not predictable from one fluorocarbon to another, especially when hydrogen is present in the fluorocarbon being purified. This is because hydrogen is frequently replaced by chlorine which reduces yield of the desired product and results in yet further impurities. In certain applications, such fluorocarbons must be especially pure, e.g. when they are used in particularly sensitive areas such as for refrigerants in air conditioners in confined areas.

It has been found that, 1,1,1,3,3,3-hexafluoropropane (HFC236fa), can be used as a replacement for the fluorocarbon $CCl_2F_2CClF_2$(CFC-114), used as a refrigerant. HFC-236fa can be prepared by numerous methods, e.g. as described in U.S. Pats. No. 5,395,997; 5,414,165; and World Patent Application WO96/15085-A1. 1,1,1,3,3,3-hexafluoropropane might be an excellent replacement for CFC-114, except that pure 1,1,1,3,3,3-hexafluoropropane has not been obtainable by known methods of preparation. This due to the fact that methods for the preparation of 1,1,1,3,3,3-hexafluoropropane result in residual impurities of other fluorocarbons. Unfortunately, some of the fluorocarbon impurities form low boiling azeotropes with 1,1,1,3,3,3-hexafluoropropane or are close boiling with 1,1,1,3,3,3-hexafluoropropane,which prevents separation by conventional distillation methods ("distillation inseparable mixtures"). Such distillation inseparable mixtures are obtained when an attempt is made to purify 1,1,1,3,3,3-hexafluoropropane by distillation from the reaction mixture in which it is made. This is especially troublesome since some of the impurities which form azeotropes or close boiling mixtures are unsaturated and cannot be tolerated to any significant extent in refrigerants in certain applications. Examples of such undesirable unsaturated fluorocarbon impurities are 1,1,1,3,3-pentafluoro-2-chloropropene obtained by the liquid phase reaction described in U.S. Pat. No. 5,395,997 and $C_3HCl_2F_3$ obtained by the vapor phase reaction described in U.S. Pat. 5,414,165.

BRIEF DESCRIPTION OF THE INVENTION

The drawing is a schematic flow diagram illustrating the method of the invention.

BRIEF DESCRIPTION OF THE INVENTION

In accordance with the invention, a method is therefore provided for the purification of 1,1,1,3,3,3-hexafluoropropane from distillation inseparable mixtures of 1,1,1,3,3,3-hexafluoropropane with at least one unsaturated fluorocarbon to obtain a 1,1,1,3,3,3-hexafluoropropane product of greater than 99.9 weight percent purity containing less than 100 parts per million of unsaturated fluorocarbons.

The method comprises:
a) reacting the mixture with chlorine to saturate the unsaturated fluorocarbons in a reacted mixture,
b) distilling the reacted mixture to obtain a 1,1,1,3,3,3-hexafluoroporpane, and
c) removing residual HCl and chlorine from the 1,1,1,3,3,3-hexafluoropropane at any point in the method subsequent to reacting the mixture with chlorine to saturate the unsaturated fluorocarbon.

The method preferably comprises:
a) reacting the distillation inseparable mixture with chlorine to saturate the unsaturated fluorocarbons,
b) washing the reacted mixture with an aqueous solution to remove residual hydrochloric acid and chlorine,
c) removing the aqueous solution, and
d) distilling the reacted mixture to obtain a 1,1,1,3,3,3-hexafluoropropane product of greater than about 99.9 weight percent purity containing less than about 100 parts per million unsaturated fluorocarbons.

The invention also includes a 1,1,1,3,3,3-hexafluoropropane product of greater than about 99.9 weight percent purity containing less than about 100 parts per million unsaturated fluorocarbons.

DETAILED DESCRIPTION OF THE INVENTION

In accordance with the invention a method is provided to purify HFC-236fa from a crude product mixture containing HFC-236fa and other saturated and unsaturated halocarbons including hydrofluorocarbons (HFC's), chlorofluorocarbons (CFC's) and hydrochlorofluorocarbons (HCFC's), any of which may be saturated or ethylenically unsaturated. The crude product can be produced by several different reaction methods as previously described. The purification method usually comprises the steps of:

1) Using conventional distillation technology to produce an azeotropic or close boiling mixture containing more than 95 weight percent HFC-236fa fluorocarbon. The balance of the mixture mainly comprises HCFC, HFC and CFC olefins (alkenes), and especially 1,1,1,3,3-pentafluoro-2-chloropropene HCFC-(1215xc).

2) Liquid phase reaction of the mixture with $Cl_2$ in the presence of a suitable catalyst or ultraviolet light (UV)

to saturate the alkenes by addition of the $Cl_2$ across the double bonds.

3) Washing of the mixture to eliminate any excess $Cl_2$ or hydrochloric acid that may have been produced by side reactions.

4) Passing the mixture through a drying medium (desiccant), such as $CaSO_4$, to remove excess water, and 5) Using conventional distillation technology to obtain a greater than 99.9 weight percent HFC-236fa product containing less than 100 ppm unsaturates.

"Fluorocarbon" as used herein means a carbon chain to which one or more fluorine atoms are attached. The carbon chain may be perfluorinated, i.e. saturated with fluorine, or may only be partially fluorinated. Partially fluorinated carbon chains may be ethylenically unsaturated, i.e. contain alkene structures, and may have attached hydrogen, chlorine, or bromine atoms. The generic term "fluorocarbon" thus includes HFC's, HCFC's and CFC's.

The crude 1,1,1,3,3,3-hexafluoropropane from initial liquid phase synthesis typically contains from about 20 to 40 weight percent fluorocarbon impurities, e.g. 1,1,1,3,3-pentafluoropropene (HFC1225zc); 1,1,1,3,3-pentafluoro-2-chloropropene (HCFC1215xc); 1,1,1,3-tetrafluoro-3-chloropropene (HCFC1224zc); 1,1-difluoro-2,2-dichloroethene HCFC1112a); trichlorofluoromethane (CFC11) and 1,1, 1,3,3-pentafluoro-3-chloropropane HCFC235fa).

The crude 1,1,1,3,3,3-hexafluoropropane obtained by liquid phase reaction is distilled to remove most impurities. The result is an azeotropic mixture of 1,1,1,3,3-pentafluoropropane and 1,1,1,3,3,3-hexafluoro-2-chloropropene with less than about 0.5 percent by weight of other fluorocarbons.

"Close boiling mixture" as used herein means a mixture of compounds which boil so close together that they vaporize at about the same temperature. Examples of such close boiling mixtures are described in U.S. Pat. 5,414,165 and comprise about 99 weight percent 1,1,1,3,3,3-hexafluoropropane, about 0.2 to about 0.7 weight percent of the unsaturated isomer of $C_3HCl_2F_3$, the balance being other fluorocarbons.

"Azeotropic mixture" as used herein means a mixture of compounds which together boil (vaporize) at a temperature lower than the boiling temperature of any of the compounds independently. The azeotrope separated by distillation from preparation by liquid phase reaction, in accordance with the present invention, may comprise about 95 weight percent or more of 1,1,1,3,3,3-hexafluoropropane and about 5 weight percent or less of fluorocarbon impurities. The most prevalent fluorocarbon impurity in the azeotrope is usually 1,1,1,3,3-pentafluoro-2-chloropropene. For example, a specific azeotropic mixture obtained by distillation from liquid phase reaction was found to contain between about 97 and about 98 weight percent 1,1,1,3,3,3 hexafluoropropane, about 0.007 weight percent 1,1,1,3,3-pentafluoropropene; between about 2 and about 3 weight percent of 1,1,1,3,3-pentafluoro-2-chloropropene; about 0.08 weight percent 1,1,-difluoro-2,2-dichloroethene; and about 0.05 weight percent of trichlorofluoromethane.

"Reacting the mixture with chlorine" means that unsaturated compounds in the distillation inseparable mixture are reacted with chlorine so that chlorine is added across double bonds of the unsaturated compounds to chlorine saturate the double bonds. Preferably the unsaturated fluorocarbons in the mixture are reacted with chlorine in the presence of ultraviolet light (UV); however, it is to be understood that chlorine may be reacted with the unsaturated fluorocarbons by other methods, e.g. catalytically. UV chlorination is usually preferred because side reactions are minimized and possible contamination by catalyst is avoided. UV reaction time may vary but is usually from about 1 to about 4 hours.

The reacting of said mixture with chlorine usually occurs in liquid phase at about atmospheric pressure at a temperature below about $-1.4°$ C. The low temperature is required since pure 1,1,1,3,3,3-hexafluoropropane boils at $-1.4°$ C. The low temperature may be maintained by any suitable method, e.g. chilled methanol or brine.

Saturating the unsaturated fluorocarbons with chlorine changes their boiling points. Therefore, after reacting with chlorine, the mixture is distilled by conventional techniques to remove remaining fluorocarbons.

Desirably, subsequent to reaction with chlorine and prior to the next distillation, residual hydrochloric acid and chlorine are usually removed even though the distillation step itself may separate the 1,1,1,3,3,3-hexafluoropropane from HCl and chlorine. This is because the removal of HCl and chlorine in the distillation step is usually not complete. Residual hydrochloric acid and chlorine, either prior to or subsequent to distillation, are usually removed by washing with an aqueous solution and then removing the aqueous solution.

"Hydrochloric acid" as used herein is intended to include hydrogen chloride (HCl), whether or not it is dissolved in water.

The chlorine reacted mixture is usually washed by blending an aqueous solution, containing acid neutralizing agents and chlorine reactants, e.g. caustic and a bisulfite, into the 1,1,1,3,3,3-hexafluoropropane mixture after chlorination, to neutralize excess chlorine and hydrochloric acid. The resulting aqueous phase is then separated from a resulting fluorocarbon phase. A major portion of the aqueous phase is usually separated by allowing the mixture of the aqueous phase and fluorocarbon phase to phase separate into an upper aqueous phase and a lower fluorocarbon phase and drawing the lower fluorocarbon phase from beneath the aqueous phase. "Caustic" means an aqueous solution comprising sodium hydroxide, potassium hydroxide or mixtures thereof. The amount of sodium or potassium hydroxide in the aqueous solution is usually from about 0.01 to about 0.5 weight percent. "Bisulfite" means any water soluble bisulfite, especially sodium and potassium bisulfites. The amount of bisulfite in the aqueous solution is usually from about 0.01 to about 0.02 weight percent. Other acid neutralizing agents such as alkaline earth hydroxides, e.g. calcium or magnesium hydroxides, can be used.

After separation of the fluorocarbon phase, it is usually contacted with a desiccant to remove residual water prior to distilling. "Desiccant" means any material which will absorb water without dissolving in or otherwise contaminating the fluorocarbon being dried, e.g. calcium sulfate or molecular sieves.

Chlorine can also be removed by reactive organics such as methyl styrene. When such a reactive organic us used, it may react with residual chlorine subsequent to the chlorine unsaturated fluorocarbon reaction and prior to washing with aqueous solution. The chlorine-chlorine reactive organic compound product may then be removed in the next distillation step.

EXAMPLE

The invention may be further illustrated by reference to the drawing which shows a schematic representation of a preferred embodiment of the method of the invention.

Stream 1 was fed into distillation column 11. Stream 1 contained crude 1,1,1,3,3,3-hexafluoropropane, prepared by liquid phase methods known to those skilled in the art as described in U.S. Pat. No. 5,395,997, previously discussed. Stream 2, exiting the top of column 11 was an azeotropic mixture of about 97.6 weight percent 1,1,1,3,3,3-hexafluoropropane and about 2.4 weight percent of 1,1,1,3,3-pentafluoro-2-chloropropene.

Stream 2 entered photochlorination reactor 21 where a 450 watt ultraviolet light source 23 was present and turned on. Stream 3 was $Cl_2$, which was sparged into reactor 21 where it added across the double bonds of unsaturated impurities, especially 1,1,1,3,3-pentafluoro-2-chloropropene. Reactor 21 was run at near atmospheric pressure (0–10 psig) and the contents were cooled using circulating chilled brine 3 a through jacket 22 of reactor 21. The reaction time was about 2 to about 4 hours. Sampling and subsequent analysis of the reactor contents confirmed when the chlorination reaction was complete. Stream 5, a slightly caustic solution containing the amount of bisulfite required to neutralize unreacted chlorine in reactor 21, was added to mixing tank 31. The amount of bisulfite used in the solution was about 0.015 weight percent and the amount of sodium hydroxide used in the solution was about 0.2%. Reacted stream 4 exited reactor 21 and was added on top of the slightly caustic bisulfite solution in tank 31. The contents of mixing tank 31 were well mixed by means of agitator 32 and any excess $Cl_2$ or hydrochloric acid were neutralized by the bisulfite and caustic, respectively.

After mixing, the agitator 32 was shut off and the contents of mixing tank 31 were allowed to phase separate into an upper aqueous phase and a lower halocarbon phase. The halocarbon phase was then removed from the bottom of mixing tank 31 as stream 6. After removal of stream 6, the aqueous phase was removed as stream 7 for treatment Stream 6 then entered drying column 41 where any residual or dissolved water was removed by $CaSO_4$ desiccant.

Dried stream 8 from drying column 41 entered distillation column 51 for separation of 1,1,1,3,3,3-hexafluoropropane from impurities. Steam 9 taken from the column 51 was greater than 99.9 weight percent 1,1,1,3,3,3-hexafluoropropane containing less than 100 ppm of unsaturated fluorocarbons. Stream 10 comprised removed impurities.

We claim:

1. A 1,1,1,3,3,3-hexafluoropropane product of greater than about 99.9 weight percent purity containing less than about 100 parts per million unsaturated fluorocarbons.

* * * * *